United States Patent
Hesse et al.

(10) Patent No.: US 6,242,632 B1
(45) Date of Patent: Jun. 5, 2001

(54) SUPPORTED CATALYSTS CONTAINING A PLATINUM GROUP METAL AND METHOD FOR PRODUCING DIARYLCARBONATES

(75) Inventors: Carsten Hesse; Ulrich Notheis, both of Tönisvorst; Johann Rechner, Kempen, all of (DE)

(73) Assignee: Bayer Aktiengesellschaft, Leverkusen (DE)

( * ) Notice: Subject to any disclaimer, the term of this patent is extended or adjusted under 35 U.S.C. 154(b) by 0 days.

(21) Appl. No.: 09/485,645

(22) PCT Filed: Aug. 5, 1998

(86) PCT No.: PCT/EP98/04861
§ 371 Date: Feb. 11, 2000
§ 102(e) Date: Feb. 11, 2000

(87) PCT Pub. No.: WO99/08786
PCT Pub. Date: Feb. 25, 1999

(30) Foreign Application Priority Data

Aug. 18, 1997 (DE) ............................................ 197 35 771

(51) Int. Cl.[7] .................................................... C07C 69/96
(52) U.S. Cl. ............................................................ 558/274
(58) Field of Search ..................................... 502/234, 324; 558/274

(56) References Cited

U.S. PATENT DOCUMENTS

| 5,336,803 | 8/1994 | Kezuka et al. | 558/277 |
| 5,380,907 | 1/1995 | Mizukami et al. | 558/270 |
| 5,750,459 | * 5/1998 | Marella et al. | 502/304 |

FOREIGN PATENT DOCUMENTS

| 0736325 | * 4/1995 | (EP) . |
| 1578713 | 11/1980 | (GB) . |
| 1-165551 | 6/1989 | (JP) . |
| 4-257546 | 9/1992 | (JP) . |
| 4-261142 | 9/1992 | (JP) . |

* cited by examiner

*Primary Examiner*—Deborah C. Lambkin
(74) *Attorney, Agent, or Firm*—Joseph C. Gil; Aron Preis

(57) ABSTRACT

A platinum metal-containing supported catalyst in which the support contains mixed oxides of metals, transition metals and semiconductor elements, which can act as redox catalysts under the reaction conditions is disclosed. Also disclosed is the preparation of these catalysts and their use in a process for preparing diaryl carbonates.

1 Claim, No Drawings

SUPPORTED CATALYSTS CONTAINING A PLATINUM GROUP METAL AND METHOD FOR PRODUCING DIARYLCARBONATES

This application is a 371 of PCT/EP98/04861 Aug. 5, 1998.

The present invention relates to platinum metal-containing supported catalysts in which the supports contain mixed oxides of metals, transition metals and semiconductor elements, which can act as redox catalysts under the reaction conditions and which have been prepared in a sol-gel process and use of the supported catalysts in a process for preparing diaryl carbonates by reacting aromatic hydroxy compounds with carbon monoxide and oxygen.

It is known that organic carbonates can be prepared by oxidative reaction of aromatic hydroxy compounds with carbon monoxide in the presence of a noble metal catalyst (DE-OS 28 15 512). Palladium is preferably used as the noble metal. In addition a co-catalyst (e.g. manganese or cobalt salts), a base, a quaternary salt, a variety of quinones or hydroquinones and a drying agent may also be used. The procedure may be performed in a solvent, preferably in methylene chloride.

In order to perform this process in an economic manner, effective recovery of the noble metal catalyst is a critical factor, in addition to the activity and selectivity of the catalyst. On the one hand the noble metal catalyst represents a large cost factor. Losses of noble metal catalyst have to be replaced at great cost. On the other hand no residues of the noble metal catalyst should remain in the product. The economic and efficient recovery of homogeneous catalysts for the process of oxidative carbonylation of aromatic hydroxy compounds to give diaryl carbonates has not hitherto been described. The separation of a noble metal catalyst from a liquid reaction mixture, e.g. by filtering or centrifuging, can be performed at low cost if heterogeneous supported catalysts are used.

In EP-A 572 980, EP-A 503 581 and EP-A 614 876 noble metal supported catalysts are used which contain 5% palladium on carbon supports. However, these types of supported catalysts produce only very unsatisfactory conversions or even none at all, so that these are also unsuitable for an economically viable process.

JP-A 01/165 551 (cited in accordance with C.A. 112:76618j (1990)) describes using palladium or palladium compounds such as palladium acetylacetonate, in combination with alkali metal or alkaline earth metal iodides or 'onium' iodides, such as tetrabutylammonium iodide, and at least one zeolite to prepare aromatic carbonates.

JP-A 04/257 546 and JP-A 04/261 142 each describe an example of a supported catalyst for preparing aromatic carbonates in which silicon carbide granules are used as the support material for a supported catalyst in a distillation column. Although drastic conditions (high pressure, high temperature) are used in the relevant examples, these catalysts produce only very low space-time yields. These low space-time yields make the economic production of aromatic carbonates with this type of supported catalyst impossible.

EP-A 736 324 describes the preparation of diaryl carbonates with heterogeneous catalysts which contain a platinum metal, preferably palladium, and a co-catalytic metal compound, preferably a metal from the group Mn, Cu, Co, Ce and Mo. When preparing the catalysts the co-catalytic metals are applied to a support.

EP-A 736 325 describes the preparation of diaryl carbonates with heterogeneous catalysts which contain a platinum metal, preferably palladium, on a support which consists of a metal oxide in which the metal may exist in several valency states.

Although these supported catalysts enable the preparation of aromatic carbonates for the first time, a further increase in activity is desirable from an economic point of view.

It has now been found that higher catalyst activities can be obtained if platinum metal-containing supported catalysts in which the support contains mixed oxides e.g. of V, Mn, Ti, Cu, La, the rare-earth metals and mixtures thereof which act as redox catalysts under the reaction conditions, which have been prepared in a sol-gel process and which contain platinum metals are used as catalysts.

The invention provides catalysts which contain (i) an oxide of the elements silicon, aluminium, titanium, zirconium or a mixture of oxides of these elements, (ii) one or more co-catalytic metal oxides from groups 4, 5, 6, 7, 11, 12, 13, 14, the iron group (atomic numbers 26 to 28) or the rare-earth metals (atomic numbers 58 to 71) in the periodic system of the elements in accordance with the new IUPAC nomenclature, and (iii) one or more platinum metals or one or more compounds of platinum metals (atomic numbers 44 to 46 and 77 and 78) in an amount 0.01 to 15 wt. %, calculated as platinum metal and with respect to the total weight of catalyst, which are obtained by preparing a gel from one or more suitable precursor(s) of the components mentioned under (i) and (ii), ageing, drying and optionally annealing the gel, shaping the mixed metal oxide obtained in this way and then applying the platinum metal component (iii) to the mixed metal oxide.

Supports according to the invention probably act like a separately added co-catalyst, but they avoid all disadvantages of separately added co-catalysts such as mixing with the reaction product and thus contaminating it. In accordance with this hypothesis, all the metals mentioned are those which can occur in several valency states. As a result of the special method of preparation, mixed oxides according to the invention are obtained which produce particularly active catalysts as compared with the prior art. This is particularly surprising since the activity of known catalysts is only very slightly affected by the method of preparation of the support.

Catalysts according to the invention contain, when ready to react (i) an oxide of the elements silicon, aluminium, titanium, zirconium or a mixture of oxides of these elements, (ii) one or more co-catalytic metal oxides of the groups 4, 5, 6, 7, 11, 12, 13, 14, the iron group (atomic numbers 26 to 28) or the rare-earth metals (atomic numbers 58 to 71) in the periodic system of the elements (IUPAC, new), and (iii) one or more platinum metals or one or more compounds of platinum metals (atomic numbers 44 to 46 and 77 and 78) in an amount 0.01 to 15 wt. %, preferably 0.05 to 10 wt. %, calculated as platinum metal and with respect to the total weight of catalyst.

Catalysts according to the invention are prepared by preparing a gel from one or more suitable precursor(s) of the components mentioned under (i) and one or more suitable precursor(s) of the components mentioned under (ii), ageing the gel, drying and optionally annealing the gel, making the mixed metal oxide obtained into the desired form, e.g. powder, granules, extrudate, spheres, cylinders, hollow rings, using methods known to a person skilled in the art, and then applying the platinum metal components to the catalyst supports being used according to the invention using methods basically known to a person skilled in the art, such as, for example, soaking, adsorption, immersion, spraying, impregnation and ion exchange.

The mixed metal oxide supports are used according to the invention as powders, tablets or binder-containing extrudates. Suitable binders are e.g. $SiO_2$, $Al_2O_3$ or aluminas. The concentration of binder may be varied over a wide range, for example 0.5 to 99.5 wt. %, with respect to the total weight of support. The mixed metal oxide may also be applied as a layer on an inert material (wash coat).

The gel according to the invention can be prepared by almost any known method. Methods which are known for preparing mixed oxides based on a gel are preferably used. This includes, for example, the hydrolysis of one or more metal alkoxides and/or hydrolysable metal compounds under acid, neutral or basic conditions in suitable solvents at temperatures of 0° C. to 200° C. In this case mixtures of different precursors of one or more elements may also be used.

Suitable precursors of silicon dioxide are alkoxides of silicon such as, for example, tetraethoxysilane, tetramethoxysilane.

Suitable precursors of aluminium oxide are lower alkoxides such as trimethoxyaluminium, triethoxyaluminium, tri-n-propoxyaluminium, tri-iso-propoxyaluminium, tri-sec-butoxyaluminium, tri-sec-butoxyaluminium, or tri-tertbutoxyaluminium or aluminium alkoxides with chelating ligands such as dibutoxyaluminium-ethylacetoacetate.

Suitable precursors of titanium oxide are tetramethoxytitanium, tetraethoxytitanium, tetraisopropoxytitanium; suitable precursors of zirconium oxide are tetraethoxyzirconium, tetra-tert-butoxyzirconium, tetra-n-butoxyzirconium, tetra-isopropoxyzirconium. Suitable hydrolysable salts are for example titanium tetrachloride, organic salts such as aluminium acetylacetonate, zirconium acetylacetonate or the corresponding mixed metal compounds and salts.

Suitable solvents are, for example, monohydric alcohols such as methanol, ethanol, n-propanol, iso-propanol, n-butanol, 2-butanol, t-butanol, polyhydric alcohols such as glycol, 1,2-propanediol, 1,3-propanediol, monofunctional or polyfunctional ketones such as acetone, 1,3-pentanedione (acetylacetone), cyclic or linear ethers with one to three oxygen atoms such as tetrahydrofuran, dioxan, diethyl ether, glycoldiethyl ether or diethyleneglycoldiethyl ether, ether-alcohols such as glycolmonomethyl ether, nitriles such as acetonitrile and benzonitrile and amides such as dimethylformamide. Alcohols, diketones and ether-alcohols are preferred. Obviously mixtures of solvents may also be used.

The solvents are used in amounts such that the molar ratio of alkoxide to solvent is 1:0.2 to 1:100.

Partially alkylated precursors $R^1_x(OR^2)_y$ may also be used in the process according to the invention, wherein M represents one of the elements mentioned under (i), (x+y) is the valency of the element and $R^1$ and $R^2$, independently of each other, represent alkyl, aralkyl or aryl groups with 1 to 20 carbon atoms. The following may be mentioned by way of example: methyltriethoxysilane, ethyltriethoxysilane.

Co-catalytic compounds which may be mentioned are one or more compounds of elements from the groups 4, 5, 6, 7, 11, 12, 13, 14, the iron group (atomic numbers 26 to 28) or the rare-earth metals (atomic numbers 58 to 71) in the periodic system of elements (IUPAC, new) with a total molar proportion of the components mentioned under (ii) of 0.1% to 99.9%, preferably 0.1% to 40%, in particular 0.5% to 20%, with respect to the total number of moles of the components mentioned under (i) and (ii), introduced into the catalyst, preferably Mn, Cu, Co, V, Nb, W, Zn, Ce, Mo, in particular Mn, Co, Cu, Mo, Ce, quite specifically Mn and/or Ce.

Suitable precursors of the co-catalytic metals are basically known, and the following may be used for example: inorganic salts such as halides, oxides, nitrates, sulphates, carboxylates, salts of monofunctional or polyfunctional organic $C_2$ to $C_{15}$ carboxylic acids such as acetates, cyclohexane butyrates, diketonates such as acetylacetonate, ethyl hexanoate, alkoxides such as methoxides, ethoxides and isopropoxides and complex compounds which contain, for example, carbon monoxide, olefins, amines, nitriles, phosphines and halides, as well as mixed salts.

Heterometallic alkoxides of the formula $[L_m$—$(OR)_2$—$M'L_n']$ are also known and are described, for example, by Mehrotra et al in Mat. Res. Soc. Symp. Proc. 121 (1988) 81; D. C. Bradley et al in "Metal Alkoxides", Academic Press, NY (1978); K. G. Caulton et al in Chem. Rev. 90 (1990) 969.

Examples of compounds containing organic ligands which may be mentioned are: cerium (IV) isopropoxide, cerium (IV) methoxyethoxide, cerium (III) acetylacetonate, cobalt carbonylmethoxide, cobalt (II) acetylacetonate, cobalt (III) acetylacetonate, manganese (II) ethoxide, manganese (II) acetylacetonate, manganese (III) acetylacetonate, copper (II) 2-ethylhexanoate, copper (II) ethoxide, copper (II) ethylacetoacetate, copper (II) acetylacetonate niobium (V) ethoxide, molybdenum (V) ethoxide (dimolybdenum decaethoxide), molybdenum (VI) oxide-bisacetylacetonate, vanadium (IV) oxide-bisacetylacetonate (vanadyl acetylacetonate), vanadium (III) acetylacetonate, vanadium triisopropoxide oxide, vanadium tri-n-propoxide oxide, tungsten (VI) ethoxide, tungsten (V) ethoxide, tungsten (VI) phenoxide, zinc (II) acetylacetonate.

Suitable platinum metal compounds are, for example, the platinum metal compounds and platinum metal-containing complex compounds described in EP-A 736 324. In the examples mentioned, palladium was mentioned as the platinum metal, but other platinum metals are also suitable such as Pt, Ir, Ru or Rh. Pd and Rh, however, are preferred, in particular Pd.

Catalysts according to the invention are prepared in at least two steps. A mixed metal oxide which does not contain any platinum metal is initially prepared using the method described above, optionally made into the required form and then the platinum metal is applied to the mixed metal oxide by methods known to a person skilled in the art.

When preparing catalysts according to the invention, a solution of the precursors of (i) and (ii) are conventionally prepared in a suitable solvent and hydrolysed with 1 to 20, preferably 1.5 to 10 mole equivalents of water, with respect to the total number of moles of compounds (i) and (ii). The water may be added in one or several portions, pure, mixed with other solvents or together with precursors of (ii) dissolved therein.

During the hydrolysis procedure, acids or bases may be added in amounts of 0.1 to 200 mol. % with respect to the total number of moles of compounds (i) and (ii).

Suitable acids are, for example, hydrochloric acid, nitric acid, sulphuric acid, formic acid, acetic acid or higher carboxylic acids with 3 to 8 carbon atoms. Di- and tricarboxylic acids with up to 8 carbon atoms are also suitable. Suitable bases are ammonia, quaternary ammonium hydroxides, $NR_4OH$, in which the R groups, independently of each other, may be alkyl, aryl or aralkyl groups with 1 to 15 carbon atoms, e.g. tetramethyl-, tetraethyl-, tetrapropyl-, tetrabutyl-, tetrapentyl- or tetraphenylammonium hydroxide, or organic nitrogen bases such as amines, pyridines, guanidines. Preferred bases are ammonia and quaternary ammonium hydroxides. The acids and bases may be used as pure substances, as anhydrous solutions or as aqueous solutions.

When adding the individual components, efficient homogenisation of the mixture should be ensured by using appropriate mixing devices such as e.g. stirrers or mixing nozzles.

If several compounds (i) and (ii) are hydrolysed, known techniques may be applied in order to mutually adjust their reactivities. The following may be mentioned by way of example: pre-hydrolysis of one compound, chemical modification of one compound with a chelating agent, the use of different alkoxide groups in the compounds and hydrolysis at different temperatures, such as is described, for example, by D. A.Ward and E. I.Ko (Ind. Eng. Chem. Res. 34 (1995) 421).

Another suitable method for preparing mixtures according to the invention from precursors of (i) and (ii) is the gelling of inorganic precursors in aqueous systems, such as the preparation of silica gels by neutralising alkali metal silicates with strong acids. Additional steps, such as washing the gel, may be required in order to wash salts which have been formed out of the mixture. During the procedure described here the precursor of (ii) may be added, for example, to one of the components before mixing the alkali metal silicate and acid.

After gelling, it is advantageous to allow the gels to age at temperatures of 20 to 100° C., preferably 20 to 80° C., for a period of at least 10 minutes. The upper limit to the ageing time is restricted only by economic factors and may be several weeks. Times between one hour and two weeks are preferred. Ageing may also be performed in several steps at different temperatures or at a temperature which changes slowly with time.

The gels are dried after they have been aged. Drying the gels may be performed by a variety of methods, depending on the method of preparation, wherein drying has an effect on the internal surface area and the pore volume of the materials.

Drying may take place on the one hand in air, under a vacuum or in a stream of gas. Suitable gases for drying the gel in a gas stream are nitrogen, oxygen, carbon dioxide or noble gases or any mixture of the gases mentioned, preferably e.g. air. Gaseous hydrocarbons for example alkanes such as methane, ethane, propane, butane, alkenes such as ethene, propene, butene, butadiene and alkynes such as ethyne, propyne, etc in any composition may also be used. Drying is performed at 0 to 300° C., preferably 20 to 250° C., in particular at 20 to 150° C. The drying time depends e.g. on the porosity of the gel and on the solvent used. It is generally a few hours, for example 0.5 to 50 h, preferably 1 to 40 h, in particular 1 to 30 h.

Another preferred method is drying under supercritical conditions such as, for example, is described by G. M. Pajonk (Applied Catalysis 72 (1991) 217) and Dutoit et al (J. Catal. 161 (1996) 651), and this leads to gels with particularly high porosities. Carbon dioxide ($T_{critical}$=31° C., $P_{critical}$=73 bar) or alcohols above their critical point (e.g. for ethanol $T_{critical}$=243° C., $P_{critical}$=63 bar), for example, may be used. Drying may be performed, batchwise, continuously or part-continuously, optionally in the presence of another inert gas.

Reduction of the platinum metal may occasionally occur during supercritical drying with alcohols and this generally has a negative effect on the activity of the catalysts according to the invention. In these cases it is recommended that the catalysts be oxidised again after drying, for example by annealing at 200 to 800° C. in a stream of gas which contains oxygen, air, halogens or hydrogen halides.

Further methods of drying, particularly for gels prepared in aqueous systems, are extractive and azeotropic drying such as are described, for example, in U.S. Pat. No. 3,887,494, US-A 3,900,457, US-A 4,169,926, US-A 4,152,503, US-A 4,436,883 or US-A 4,081,407.

After drying the dried mixed oxides may be calcined. This may take place, in the case of mixed oxides prepared in several steps, either before or after applying the platinum metal, or several times. Calcining may take place in air, under vacuum or in a gas stream. Suitable gases for calcining mixed oxides in a gas stream are e.g. nitrogen, oxygen, carbon dioxide or noble gases and any mixtures of the gases mentioned, preferably air. Calcining is performed at 100 to 800° C., preferably at 100 to 700° C., in particular at 100 to 600° C. It may sometimes be of advantage if the composition of the gas is altered either suddenly or continuously during calcination. The calcining time is generally a few hours, for example 0.5 to 50 h, preferably 1 to 40 h, in particular 1 to 30h.

In a preferred variant of the method of preparing the catalyst, the platinum metal is applied to the previously-prepared metal mixed oxide. Methods may be used for this which are basically known to a person skilled in the art and are described, for example, in EP-A 736 325. The mixture may be stirred during application of the platinum metal to the metal mixed oxide. However, it may also be advantageous to allow the mixture to stand or to shake it.

After applying platinum metal to the support, the supported catalyst is isolated, e.g. by filtering, sedimentation or centrifuging. In a further embodiment of the invention the solvent is separated by distillation.

After separating the solvent, the supported catalysts obtained in this way are dried. The drying procedure is preferably performed in air, under vacuum, or in a gas stream under the conditions given above for drying the gels. A calcination step may be performed under the conditions described above, after the drying procedure.

It is also possible to apply the mixed oxides according to the invention as a layer on other catalyst supports. Suitable support materials for the application of a layer of metal mixed oxide are any industrially conventional catalyst supports based on carbon, oxides of elements, carbides of elements or salts of elements in a variety of forms. Examples of carbon-containing supports are coke, graphite, carbon black or active carbon. Examples of elemental oxide catalyst supports are $SiO_2$ (natural or synthetic silicas, quartz), $Al_2O_3$ in a variety of modifications ($\alpha, \gamma, \delta, \eta, \theta$), aluminas, natural and synthetic aluminosilicates (zeolites), $TiO_2$ (rutile, anatase), $ZrO_2$ or ZnO. Examples of elemental carbides and salts are SiC, $AlPO_4$, $BaSO_4$, $CaCO_3$, etc. They may be used either as chemically uniform pure substances or as mixtures. Particulate or powdered materials, or even monoliths, are suitable for use according to the invention. Particulate materials are particularly preferred.

The invention also provides a process for preparing an organic carbonate by reacting an aromatic hydroxy compound with carbon monoxide and oxygen in the presence of the catalysts according to the invention, a quaternary ammonium or phosphonium salt and a base.

The organic carbonate prepared by the process according to the invention corresponds to the formula

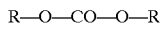   (I)

in which

R represents a substituted or non-substituted $C_6$–$C_{12}$ aryl group, preferably a substituted or non-substituted phenyl group, in particular a non-substituted phenyl group.

Aromatic hydroxy compounds which may be used according to the invention correspond to the formula

R—O—H                    (II)

in which R is defined as above. Aromatic hydroxy compounds which can be reacted using the supported catalysts according to the invention are for example phenol, o-, m- or p-cresol, o-, m- or p-chlorophenol, o-, m- or p-ethylphenol, o-, m- or p-propylphenol, o-, m- or p-methoxyphenol, 2,6-dimethylphenol, 2,4-dimethylphenol, 3,4-dimethylphenol, 1-naphthol, 2-naphthol or bisphenol-A, preferably phenol. The aromatic hydroxy compound may be substituted with one or two substituents such as a $C_1$–$C_4$ alkyl group, a $C_1$–$C_4$ alkoxy group, fluorine, chlorine or bromine.

Catalysts according to the invention may be used as powders, moulded items or monoliths, preferably as powders or moulded items, and are separated from the reaction mixture by e.g. filtration, sedimentation or centrifuging.

Preparation of aromatic carbonates using supported catalysts according to the invention may be performed in a variety of ways. One possibility is a batchwise process. In the event of a continuous mode of operation in either a counter-flow or parallel flow system, or in the trickle phase on a fixed bed catalyst, loads of 0.01 to 20 g of aromatic hydroxy compound per gram of supported catalyst per hour, preferably 0.05 to 10 g of aromatic hydroxy compound per gram of supported catalyst per hour, in particular 0.1 to 5 g of aromatic hydroxy compound per gram of supported catalyst per hour are used. The supported catalyst used in batchwise trials may be used repeatedly with the same feed materials without any purification. With a continuous mode of operation the supported catalysts used may remain in the reactor for a long time. A continuous mode of operation in a single reactor or in a cascade of reactors are preferably used when using supported catalysts according to the invention.

If the supported catalyst is used as a powder, the stirred container to be used for mixing the reaction components is fitted with stirrers which can be used for this purpose. When working with supported catalyst powders as a suspension in stirred vessels or bubble columns, amounts of 0.001 to 50 wt. %, preferably 0.01 to 20 wt. %, in particular 0.1 to 10 wt. % of supported catalyst powder, with respect to the amount of aromatic hydroxy compound used, are used. In particularly preferred embodiments, the heterogeneous supported catalyst is used as moulded items fixed in place in stirred tanks, bubble columns, trickle phase reactors or cascades of these reactors, wherein different types of reactors may also be used in combination in a cascade.

In the event that the catalyst is arranged as a fixed bed, the catalyst is preferably used as moulded items, e.g. as spheres, cylinders, small rods, hollow cylinders, rings, etc. If required, catalysts may be modified further by extruding, making tablets, optionally adding further catalyst supports or binders such as $SiO_2$ or $Al_2O_3$, and calcining. The preparation and further processing of catalysts used according to the invention are generally known to a person skilled in the art and are part of the prior art.

In the process according to the invention any organic or inorganic bases or mixtures of these may be used. Examples of inorganic bases which may be mentioned, without restricting the process according to the invention, are alkali metal hydroxides and carbonates, carboxylates or other salts of weak acids and alkali metal salts of aromatic hydroxy compounds of the formula (II), e.g. alkali metal phenolates. Obviously the hydrates of alkali metal phenolates may also be used in the process according to the invention. An example of this type of hydrate which may be mentioned here, without restricting the process according to the invention, is sodium phenolate trihydrate. The amount of added water, however, is preferably such that a maximum of 5 moles of water are used per mole of base. Higher amounts of water lead, inter alia, to poorer conversions and decomposition of the carbonates being formed. Examples of organic bases which may be mentioned, without restricting the process according to the invention, are tertiary amines which may have $C_6$–$C_{10}$ aryl, $C_7$–$C_{12}$ aralkyl and/or $C_1$–$C_{20}$ alkyl groups as organic groups, or pyridine bases or hydrogenated pyridine bases, for example triethylamine, tripropylamine, tributylamine, trioctylamine, benzyldimethylamine, dioctylbenzylamine, dimethylphenethylamine, 1-dimethylamino-2-phenylpropane, pyridine, N-methylpiperidine, 1,2,2,6,6,-pentamethylpiperidine. An alkali metal salt of an aromatic hydroxy compound is preferably used as the base, in particular an alkali metal salt of the aromatic hydroxy compound which is also being reacted to give the organic carbonate. This alkali metal salt may be a lithium, sodium, potassium, rubidium or caesium salt. Lithium, sodium and potassium phenolate are preferably used, in particular sodium phenolate.

The base may be added to the reaction mixture as the pure compound in solid form or as molten material. In a further embodiment of the invention the base is added to the reaction mixture as a solution which contains 0.1 to 80 wt. %, preferably 0.5 to 65 reaction mixture as a solution which contains 0.1 to 80 wt. %, preferably 0.5 to 65 wt. %, in particular 1 to 50 wt. % of the base. Solvents which may be used for this are either alcohols or phenols such as e.g. the phenol participating in the reaction or also inert solvents. Examples are those mentioned below for use as reaction media. These solvents may be used individually or in any combination with each other. Thus there is one embodiment of the process according to the invention, for example, in which the base is dissolved in a molten phenol which has been diluted with a solvent. The base is preferably dissolved in a molten aromatic hydroxy compound, in particular in the molten aromatic hydroxy compound which is intended to be reacted to give the organic carbonate. Quite specifically the base is dissolved in phenol. The base is added in an amount which does not depend on the stoicheiometry. The ratio of platinum metal, e.g. palladium, to base is preferably chosen so that 0.1 to 500, preferably 0.3 to 200, in particular 0.9 to 130 equivalents of base, with respect to platinum metal, e.g. palladium, are used per mole of platinum metal, e.g. palladium.

The process according to the invention is preferably performed without using a solvent. Obviously inert solvents may also be used. Examples of solvents which may be mentioned are dimethylacetamide, N-methylpyrrolidinone, dioxan, t-butanol, cumyl alcohol, isoamyl alcohol, tetramethylurea, diethyleneglycol, halogenated hydrocarbons (e.g. chlorobenzene or dichlorobenzene) and ethers.

The quaternary salts used in the context of the present invention may be, for example, ammonium or phosphonium salts substituted with organic groups. Compounds suitable for use in the process according to the invention are ammonium and phosphonium salts which contain, as organic groups, $C_6$–$C_{10}$ aryl, $C_7$–$C_{12}$ aralkyl and/or $C_1$–$C_{20}$ alkyl groups and, as anion, a halide, tetrafluoroborate or hexafluorophosphate. Ammonium salts which are preferably used in the process according to the invention contain, as organic groups, $C_6$–$C_{10}$ aryl, $C_7$–$C_{12}$ aralkyl and/or $C_1$–$C_{20}$ alkyl groups and, as anion, a halide, in particular tetrabutylammonium bromide. The amount of this type of quaternary salt is 0.1 to 50 wt. %, with respect to the weight of the reaction mixture. This amount is preferably 0.5 to 15 wt. %, in particular 1 to 5 wt. %.

The process according to the invention, preferably without a solvent, is performed at 30 to 200° C., preferably 30 to 150° C., in particular 40 to 120° C. at a pressure of 1 to 100 bar, preferably 2 to 50 bar, in particular 5 to 25 bar.

EXAMPLES

Comparison Example 1
(In Accordance with EP-A 736 324)
Preparing a Powdered Manganese Oxide Support:

85 g of sodium hydroxide (2.125 mol) dissolved in 200 ml of water were added dropwise to a solution of 126 g of manganese (II) chloride (1 mol) in 500 ml of water. The precipitate obtained in this way was filtered under suction, washed and dried. Then it was annealed for 3 h at 300° C. and for 2 h at 500° C.

Coating the Powdered Manganese Oxide with Palladium:

300 ml of a solution of 50 g of sodium tetrachloropalladate (II) hydrate containing 15 % palladium in water were added to a slurry of 292.5 g of manganese dioxide powder in 1500 ml of water at room temperature. The mixture was adjusted to be alkaline using dilute caustic soda. The suspension was filtered under suction and dried at 100° C. The heterogeneous catalyst contained 2.5% palladium on an $MnO_2$ support, calculated as metal.

Use of the Supported Catalyst to Prepare Diphenyl Carbonate:

8.31 g of tetrabutylammonium bromide and 0.77 g of manganese (II) acetylacetonate dissolved in 450 g of phenol were introduced into an autoclave (1 litre) with a gas dispersion stirrer and condenser and with a cold trap connected in series. Then 4 g of the supported catalyst described above and 2.21 g of sodium phenolate dissolved in 50 g of phenol were added. The pressure was then adjusted to 14 bars by introducing a gaseous mixture of carbon monoxide and oxygen (95:5 vol. %). The amount of gaseous mixture was adjusted to 350 Nl/h. A sample was withdrawn from the reaction mixture each hour and analysed gas chromatographically. The analyses showed that after 1 h 9.9% of diphenyl carbonate, after 2 h 15.2% of diphenyl carbonate and after 3 h 18.2 % of diphenyl carbonate were present in the reaction mixture. 11.8 g of a phenol/water mixture had condensed in the cold trap.

Comparison Example 2
(In Accordance with EP-A 736 325)
Coating a Powdered Titanium Dioxide with Palladium and Manganese:

300 ml of a solution of 40.5 g (0.16 mol) of manganese (II) nitrate tetrahydrate in water were added to a slurry of 283.5 g of titanium dioxide powder (Norton) in 1500 ml of water at room temperature. The mixture was then made alkaline with dilute caustic soda solution. The suspension was filtered under suction, washed with water, dried at 100° C. and annealed for 3 h at 300° C. The support, doped with manganese, was slurried in 1500 ml of water and then 300 ml of solution containing 50 g of sodium tetrachloropalladate (II) hydrate containing 15% of palladium were added. The mixture was adjusted to be alkaline with dilute caustic soda solution. The suspension was filtered under suction, washed and dried at 100° C.

The catalyst contained 2.5% palladium and 3% manganese, each calculated as the metal.

Use of the Supported Catalyst to Prepare Diphenyl Carbonate:

The supported catalyst was used to prepare diphenyl carbonate in the same way as described in comparison example 1. The analyses showed that after 1 h 9.6% of diphenyl carbonate, after 2 h 16.1% diphenyl carbonate and after 3 h 21.0% diphenyl carbonate were present in the reaction mixture. 12.3 g of phenol/water mixture had condensed in the cold trap.

Example 1
Preparing a Si/Mn co-gel and Coating with Palladium 5.2 g of $Mn(acac)_3$ were dissolved in 200 ml of ethanol in a polypropylene beaker and mixed with 100 ml of tetraethoxysilane. 36 ml of 8N HCl were added to the mixture with stirring over the course of 18 minutes. The mixture was covered loosely with paper and allowed to stand for 6 days at room temperature to gel. Then the gel was dried for 2 days at 40° C. in a vacuum drying cabinet, milled to give a powder and the powder was annealed for 3 h at 300° C. in air.

0.54 g of $Pd(acac)_2$ were dissolved in 100 g of acetylacetone, the dried and powdered gel was added thereto and stirred for 1 h at 50° C. on a Rotavapor. The solvent was then distilled off and the catalyst dried overnight at 110° C. under vacuum in a drying cabinet.

The catalyst contained 0.7% palladium and 3% manganese, each calculated as the metal.

Use of the co-gel Catalyst to Prepare Diphenyl Carbonate

The trial was performed in the same way as described in comparison example 1, but with the difference that 14.3 g of catalyst were used. Analysis showed that after 1 h 12 % diphenyl carbonate, after 2 h 17.6% diphenyl carbonate and after 3 h 24.1% diphenyl carbonate were present in the reaction mixture. 14.1 g of a phenol/water mixture had condensed in the cold trap.

Example 2
Preparing a Si/Mn co-gel and Coating with Palladium 5.2 g of $Mn(acac)_3$ were dissolved in 200 ml of ethanol in a polypropylene beaker and mixed with 100 ml of tetraethoxysilane. 36 ml of 8N HCl were added to the mixture with stirring over the course of 18 minutes. The mixture was covered loosely with paper and allowed to stand for 3 weeks at room temperature to gel. Then the gel was dried for 2 days at 40° C. in a vacuum drying cabinet, milled to give a powder and the powder was annealed for 3 h at 300° C. in air.

0.54 g of $Pd(acac)_2$ were dissolved in 100 g of acetylacetone, the dried and powdered gel was added thereto and stirred for 1 h at 50° C. on a Rotavapor. The solvent was then distilled off and the catalyst dried overnight at 110° C. under vacuum in a drying cabinet.

The catalyst contained 0.7% palladium and 3% manganese, each calculated as the metal.

Use of the co-gel Catalyst to Prepare Diphenyl Carbonate

The supported catalyst was used to prepare diphenyl carbonate in the same way as in example 1. Analysis showed that after 1 h 14.0% diphenyl carbonate, after 2 h 20.6% diphenyl carbonate and after 3 h 26.7% diphenyl carbonate were present in the reaction mixture. 16.7 g of a phenol/water mixture had condensed in the cold trap.

Example 3
Preparing a Si/Mn co-gel and Coating with Palladium 10.4 g of $Mn(acac)_3$ were dissolved in 200 ml of ethanol in a polypropylene beaker and mixed with 100 ml of tetraethoxysilane. 36 ml of 8N HCl were added to the mixture with stirring over the course of 18 minutes. The mixture was covered loosely with paper and allowed to stand for 6 days at room temperature to gel. Then the gel was dried for 2 days at 40° C. in a vacuum drying cabinet, milled to give a powder and the powder was annealed for 3 h at 300° C. in air.

1.76 g of sodium tetrachloropalladate trihydrate were dissolved in 100 g of water, the dried and powdered gel was added thereto and stirred for 2 h at 60° C. on a Rotavapor. The solvent was then distilled off and the catalyst dried overnight at 110° C. under vacuum in a drying cabinet.

The catalyst contained 2.0% palladium and 6% manganese, each calculated as the metal.

Use of the co-gel Catalyst to Prepare Diphenyl Carbonate

The supported catalyst was used to prepare diphenyl carbonate in the same way as in example 2, with the difference that 5.0 g of catalyst were used. Analysis showed that after 1 h 16.4% diphenyl carbonate, after 2 h 22.0% diphenyl carbonate and after 3 h 27.2% diphenyl carbonate were present in the reaction mixture. 12.1 g of a phenol/water mixture had condensed in the cold trap.

Example 4

Preparing a Si/Mn co-gel and Coating with Palladium 10.4 g of $Mn(acac)_3$ were dissolved in 200 ml of ethanol in a polypropylene beaker and mixed with 100 ml of tetraethoxysilane. A solution of 1.8 g of glacial acetic acid in 27 g of distilled water was added to the mixture with stirring. The mixture was covered loosely with paper and allowed to stand for 10 days at room temperature to gel. Then the gel was dried for 2 days at 40° C. in a vacuum drying cabinet, milled to give a powder and the powder was annealed for 3 h at 300° C. in air.

0.77 g of $Pd(acac)_2$ were dissolved in 100 g of acetylacetone, the dried and powdered gel was added thereto and stirred for 1 h at 50° C. on a Rotavapor. The solvent was then distilled off and the catalyst dried overnight at 110° C. under vacuum in a drying cabinet.

The catalyst contained 1.0% palladium and 6% manganese, each calculated as the metal.

Use of the co-gel Catalyst to Prepare Diphenyl Carbonate

The supported catalyst was used to prepare diphenyl carbonate in the same way as in example 3, with the difference that 10.0 g of catalyst were used. Analysis showed that after 1 h 11.9% diphenyl carbonate, after 2 h 18.3% diphenyl carbonate and after 3 h 24.3% diphenyl carbonate were present in the reaction mixture. 12.1 g of a phenol/water mixture had condensed in the cold trap.

Example 5

Preparing a Al/Mn co-gel and Coating with Palladium 50 g of aluminium sec-butylate were mixed with 200 ml of 2-butanol and a solution of 6.6 g $Mn(acac)_3$ in 100 ml of warm acetone was added thereto. The mixture was heated to 40° C. and a mixture of 10 ml of distilled water in 100 ml of methanol was added slowly with stirring on a Rotavapor. After one hour the mixture was heated to 60° C. and stirred for 20 h at this temperature. The solvent was distilled off, the residue dried overnight at 110° C. in a vacuum drying cabinet, and then dried for 3 h at 350° C. in a stream of air.

0.42 g of $Pd(acac)_2$ were dissolved in 100 g of acetylacetone, the dried and powdered gel was added thereto and stirred for 1 h at 50° C. on a Rotavapor. The solvent was then distilled off and the catalyst dried overnight at 110° C. under vacuum in a drying cabinet.

The catalyst contained 0.7% palladium and 5% manganese, each calculated as the metal.

Use of the co-gel Catalyst to Prepare Diphenyl Carbonate

The supported catalyst was used to prepare diphenyl carbonate in the same way as in example 2. Analysis showed that after 1 h 11.9% diphenyl carbonate, after 2 h 17.6% diphenyl carbonate and after 3 h 23.7% diphenyl carbonate were present in the reaction mixture. 13.5 g of a phenol/water mixture had condensed in the cold trap.

Example 6

Preparing a Zr/Mn co-gel and Coating with Palladium 12.1 g of $Mn(acac)_3$ were dissolved in 600 ml of ethanol in a polypropylene beaker and under a nitrogen atmosphere and then 143 g of a 70% strength solution of zirconium n-propoxide were added. A mixture of 12 ml of distilled water and 13 g 8N HCl (25.7 wt. %) were added slowly to the mixture with stirring. The mixture was covered loosely with paper and allowed to stand for 7 days at room temperature to gel. Then the gel was dried for 2 days at 40° C. in a vacuum drying cabinet, milled to give a powder and the powder was annealed for 7 h at 450° C. in air.

0.86 g of $Pd(acac)_2$ were dissolved in 100 g of acetylacetone, the dried and powdered gel was added thereto and stirred for 1 h at 50° C. on a Rotavapor. The solvent was then distilled off and the catalyst dried overnight at 110° C. under vacuum in a drying cabinet.

The catalyst contained 0.7% palladium and 5% manganese, each calculated as the metal.

Use of the co-gel Catalyst to Prepare Diphenyl Carbonate

The supported catalyst was used to prepare diphenyl carbonate in the same way as in example 5. Analysis showed that after 1 h 10.2% diphenyl carbonate, after 2 h 16.8% diphenyl carbonate and after 3 h 21.3% diphenyl carbonate were present in the reaction mixture. 13.4 g of a phenol/water mixture had condensed in the cold trap.

Example 7

Preparing a Si/Mn co-gel and Coating with Palladium 5.2 g of $Mn(acac)_3$ were dissolved in 200 ml of ethanol in a polypropylene beaker and mixed with 100 ml of tetraethoxysilane. 44 ml of a 25% strength aqueous ammonia solution were added to the mixture with stirring. The mixture was covered loosely with paper and allowed to stand for 7 days at room temperature to gel. Then the gel was dried for 3 days at 40° C. in a vacuum drying cabinet, milled to give a powder and the powder was annealed for 6 h at 500° C. in air.

1.16 g of $Pd(acac)_2$ were dissolved in 100 g of acetylacetone, the dried and powdered gel was added thereto and stirred for 1 h at 50° C. on a Rotavapor. The solvent was then distilled off and the catalyst dried overnight at 110° C. under vacuum in a drying cabinet.

The catalyst contained 1.5% palladium and 3% manganese, each calculated as the metal.

Use of the co-gel Catalyst to Prepare Diphenyl Carbonate

The supported catalyst was used to prepare diphenyl carbonate in the same way as in example 1, with the difference that 6.7 g of catalyst were used. Analysis showed that after 1 h 12.8% diphenyl carbonate, after 2 h 18.5% diphenyl carbonate and after 3 h 25.6% diphenyl carbonate were present in the reaction mixture. 15.6 g of a phenol/water mixture had condensed in the cold trap.

Example 8

Preparing a Si/Mn/Ce co-gel and Coating with Palladium 10.4 g of $Mn(acac)_3$ were dissolved in 200 ml of ethanol in a polypropylene beaker and mixed with 100 ml of tetraethoxysilane. A solution of 0.12 g of cerium (III) acetate in 39 ml of 8N HCl was added to the mixture with stirring over the course of 20 minutes. The mixture was covered loosely with paper and allowed to stand for 8 days at room temperature to gel. Then the gel was dried for 2 days at 40° C. in a vacuum drying cabinet, milled to give a powder and the powder was annealed for 3 h at 300° C. in air.

1.16 g of Pd(acac)$_2$ were dissolved in 100 g of acetylacetone, the dried and powdered gel added thereto and stirred for 1 h at 50° C. on a rotavapor. The solvent was then distilled off and the catalyst dried overnight at 110° C. under vacuum in a drying cabinet.

The catalyst contained 1.5% palladium, 0.2% cerium and 6% manganese, each calculated as the metal.

Use of the co-gel Catalyst to Prepare Diphenyl Carbonate

The supported catalyst was used to prepare diphenyl carbonate in the same way as in example 7. Analysis showed that after 1 h 9.1% diphenyl carbonate, after 2 h 15.8% diphenyl carbonate and after 3 h 23.1% diphenyl carbonate were present in the reaction mixture. 14.2 g of a phenol/water mixture had condensed in the cold trap.

What is claimed is:

1. A Process for preparing an organic carbonate comprising
   (A) obtaining a supported catalyst by a process comprising
      (i) preparing a gel containing at least one member selected from a first group consisting of silicon oxide, aluminum oxide, titanium oxide and zirconium oxide and at least one member selected from a second group consisting of metal oxides of the elements of groups 4, 5, 6, 7, 11, 12, 13, 14, the iron group (atomic numbers 26 to 28) and the rare-earth metals (atomic numbers 58 to 71), and
      (ii) aging said gel to obtain an aged gel,
      (iii) drying said aged gel to obtain dry mixed metal oxides,
      (iv) shaping said dry mixed metal oxides to obtain a shaped mixed metal oxide and
      (v) applying at least one platinum metal component selected from the group consisting of platinum metals (atomic numbers 44 to 46 and 77 and 78) and compound of said platinum metals to said shaped metal oxide, in an amount 0.01 to 15 wt. %, calculated as platinum metal with respect to the total weight of said supported catalyst, to obtain a supported catalyst and
   (B) reacting an aromatic hydroxy compound with carbon monoxide and oxygen in the presence of said supported catalyst.

* * * * *